(12) United States Patent
Davis et al.

(10) Patent No.: US 6,767,989 B2
(45) Date of Patent: Jul. 27, 2004

(54) PHOSPHORUS COMPOUNDS

(75) Inventors: Keith Philip Davis, Staffordshire (GB); Graham Philip Otter, Birmingham (GB); Gary Woodward, Cheshire (GB)

(73) Assignee: Rhodia Consumer Specialties Limited, Oldbury (GB)

( * ) Notice: Subject to any disclaimer, the term of this patent is extended or adjusted under 35 U.S.C. 154(b) by 0 days.

(21) Appl. No.: 10/182,880

(22) PCT Filed: Jan. 31, 2001

(86) PCT No.: PCT/GB01/00374
§ 371 (c)(1),
(2), (4) Date: Oct. 9, 2002

(87) PCT Pub. No.: WO01/57050
PCT Pub. Date: Aug. 9, 2001

(65) Prior Publication Data
US 2003/0073805 A1 Apr. 17, 2003

(30) Foreign Application Priority Data
Feb. 2, 2000  (GB) .............................................. 0002278
May 11, 2000 (GB) .............................................. 0011240

(51) Int. Cl.$^7$ ............................. C08G 79/02; C07F 9/30
(52) U.S. Cl. ......................................... 528/398; 562/20
(58) Field of Search ........................ 558/70, 155, 156, 558/161; 562/8, 20; 528/398

(56) References Cited

U.S. PATENT DOCUMENTS

| | | | | |
|---|---|---|---|---|
| 2,957,931 A | * | 10/1960 | Hamilton et al. | ............. 554/78 |
| 3,734,954 A | * | 5/1973 | Maier | ............. 562/19 |
| 4,733,005 A | * | 3/1988 | Schmidt et al. | ............. 560/222 |
| 5,647,995 A | | 7/1997 | Kneller et al. | |
| 5,783,728 A | * | 7/1998 | Kneller et al. | ............. 562/21 |
| 6,071,434 A | * | 6/2000 | Davis et al. | ............. 252/389.2 |

FOREIGN PATENT DOCUMENTS

| | | | |
|---|---|---|---|
| DE | 199 12920 | * | 9/2000 |
| EP | 0 861 846 A A | | 9/1998 |
| WO | WO 00/56741 | * | 9/2000 |

OTHER PUBLICATIONS

CA:76:34351 abs of Phosphorus and the Related Group V Elements by Maier et al 1(3) pp 105–9 1971.*
CA:100>121239 abs of Khimiko–Farmatsevticheskii Zhurnal by Yudelevich et al 17(12) pp 1448–53 1983.*

* cited by examiner

*Primary Examiner*—Jean F. Vollano
(74) *Attorney, Agent, or Firm*—Frishauf, Holtz, Goodman & Chick, P.C.

(57) ABSTRACT

Compounds of formula (I), wherein each of R and R' are independently selected from hydrogen, a hydroxyl group, a carboxyl group, an alkyl, aryl or alkaryl group or a hydroxy or carboxy substituted alkyl, aryl or alkaryl group, provided that R and R', together have a total of less than 23 carbon atoms, R" may either be hydrogen or a CHR=CR$^1$ group or be selected from the same categories as R'"; R'" is a group, or polymeric chain comprising from 1 to 100,000 groups, said group or groups being derived form at least one ethylenically unsaturated compound wherein the double bond is activated by an adjacent electron withdrawing group, and n is greater than 1 are novel, are useful corrosion inhibitors and are valuable intermediates in preparing telomers for use in water treatment.

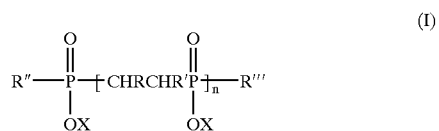

22 Claims, No Drawings

PHOSPHORUS COMPOUNDS

This application is a U.S. National Phase Application under 35 USC 371 of International Application PCT/GB01/00374 (published in English) filed Jan. 31, 2001, now WO 01/57050.

The present invention concerns novel phosphorus compounds which may be obtained by a process comprising reacting an acetylenic compound with hypophosphorous acid, or its salts.

The reaction of acetylene with hypophosphorous acid in the presence of perbenzoic acid or tertiary butyl peroxide to give 1,2-diphosphino ethane was described by Nifantev et al in Zh Obstich Khim Vol 56 Pp 773–781 (1986). The Authors state that the reaction product with two organic groups attached to the phosphorus was not obtained. This clearly implies that no polymeric material could be obtained by the method described.

Kneller et al (U.S. Pat. No. 5,647,995) describe the preparation of homologues and substituted analogues of 1,2-diphosphino ethane by reacting hypophosphorous acid with higher alkynes and substituted alkynes. The preparation of mono and diphosphinates is described but no copolymers of acetylene with hypophosphorous acid containing more than 2 phosphorus atoms per molecule were prepared or described. Kneller et al also describe reacting the mono or diphosphinates with unsaturated carboxylic acids such as acrylic acid to make telomers which are useful in water treatment as scale inhibitors of calcium carbonate scale.

We have now discovered that contrary to the teaching of Nifantev et al, the reaction between hypophosphorous acid and alkynes can be used to prepare polymers with more than two alkylene groups and more than two phosphorus atoms. Such polymers are particularly useful as corrosion inhibitors and/or as intermediates, for the synthesis of a variety of water treatment agents, fire retardants, tanning agents and biocides. The reaction with acetylene proceeds with difficulty and requires relatively extreme conditions to obtain a high degree of polymerisation, however higher alkynes and substituted alkynes, containing 3 to 25 carbon atoms, react more readily.

In a first embodiment, the present invention provides a compound of the formula (1):

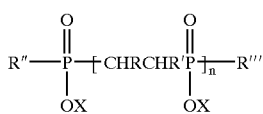

(I)

wherein:
R and R' are each independently selected from hydrogen, a hydroxyl group, a carboxyl group, an alkyl, aryl or alkaryl group or a hydroxy- or carboxy-substituted alkyl, aryl or alkaryl group, provided that R and R' together have a total of less than 23 carbon atoms;
R" is hydrogen, or CHR=CR' or selected from the same categories as R'";
R'" is a group, or a polymeric chain comprising from 1 to 100,000 groups, each said group being derived from at least one ethylenically unsaturated compound wherein the double bond is activated by an adjacent electron-withdrawing group;
X is hydrogen or a cation or an alkyl group; and n is greater than 1.

According to another embodiment our invention provides a method of producing a compound of the type described in the immediately-preceding paragraph, said method comprising the copolymerisation of hypophosphorous acid or a salt or ester of said acid with an acetylenic compound of formula RC≡CR', where R and R' (which may be the same or different) are each selected from hydrogen, a hydroxy group, a carboxy group, an alkyl, aryl or alkaryl group or a hydroxy- or carboxy-substituted alkyl, aryl or alkaryl group having from 1 to 22 carbon atoms, so that R and R' together have from 0 to 25 carbon atoms, whereby in said formula (I) R" and R'" are each hydrogen and the average value of n is greater than one.

According to a further embodiment the invention provides the use of said polymer as a corrosion inhibitor and/or scale inhibitor in the treatment of a water system.

According to a fourth embodiment the invention provides a method of preparing a telomer which comprises reacting said polymer with an ethylenically unsaturated compound wherein the double bond is activated by an adjacent electron withdrawing group.

According to a fifth embodiment the invention provides a method of treating potentially corrosive and/or scale forming water systems which comprises adding a corrosion or scale inhibiting proportion of said polymer and/or said telomer to said system.

Preferably the reaction is carried out in a solvent capable of dissolving both reagents. Depending on the acetylenic compound, the solvent may be water or a polar organic solvent, typically in admixture, with aqueous hypophosphorous acid, eg: ethanol, dioxan, a water miscible glycol or glycol ether such as ethylene glycol or ethylene glycol monomethyl ether, ketones such as acetone or methyl isobutyl ketone, or diethyl formamide. The reaction also requires an initiator, which may preferably be a source of free radicals such as hydrogen peroxide, sodium persulphate, azo compounds such as azoisobutyronitrile, organic peroxides or a source of ultraviolet or ionising radiation.

The acetylenic compound may be acetylene itself, which may, for example, be bubbled through a solution of hypophosphorous acid or its salts. However good yields of higher polymers are not readily obtainable from acetylene itself due to its volatility, which may require conditions such as high pressure which are inconvenient or potentially hazardous. We therefore prefer to use less volatile acetylenic compounds, and especially alkynes and hydroxy or carboxy alkynes with 3 to 25 carbon atoms, such as propargyl alcohol, acetylene dicarboxylic acid or an alkyne having, preferably 3 to 20 carbon atoms such as 1-butyne, 2-butyne or a $C_{12-14}$ alkyne. It is also within the scope of the invention to use cyclic alkynes, eg: in which R and R1 in the foregoing formula together with the acetylenic group form a cycloalkyne ring.

The reaction may be carried out at an elevated temperature, eg: 40 to 100° C. preferably 50 to 70° C.

The proportions may be substantially equal or may comprise a small, eg: up to 20%, stoichiometric excess of either reagent but preferably of the hypophosphite. The reaction may be carried out under elevated, atmospheric or, preferably, reduced pressure.

The hypophosphorous reagent may be the acid or a soluble salt such as sodium, potassium or ammonium or an ester such as the methyl, ethyl or isopropyl ester.

The present invention further provides a polymer, of the formula (II):

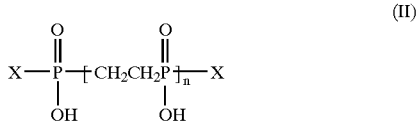

(II)

where X is hydrogen or a cation or alkyl group, n is from 1.05 to 100, e.g.: 1.2 to 50, preferably 1.5 to 25 especially 2 to 20 more especially 3 to 15.

It is also possible to obtain polymers containing, e.g.:

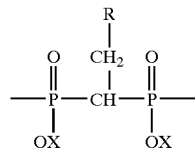

units, especially when R is a bulky group e.g.: a phenyl group.

According to a further embodiment, the invention provides a compound comprising a telomer of the formula (III):

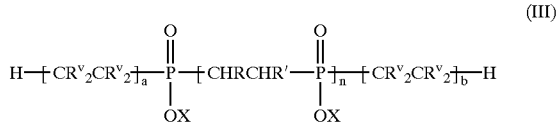

(III)

where X, R, R' have the same significance as before, at least one $R^v$, in each monomer unit is a hydroxy, carboxy, sulpho, phosphono, amido, aceto, or aryl group or halogen, and each other $R^v$ is independently selected from hydrogen, and $C_{1-4}$ alkyl, carboxyl, sulpho, phosphono, hydroxyl groups, and carboxy, sulpho, phosphono or hydroxy substituted $C_{1-4}$ alkyl groups, (a+b) is from 5 to 200 and n is greater than 1.

The novel telomers may be prepared by co-polymerising said polymers with at least one monomer of formula $R_2{}^v$=$CR_2{}^v$ where $R^v$ has the same significance as before, in the presence of a free radical initiator.

Preferred monomers include acrylic acid, fumaric acid, maleic acid, vinylsulphonic acid, vinyl phosphonic acid, vinylidene diphosphonic acid, methacrylic acid, itaconic acid, aconitic acid, mesaconic acid, citraconic acid, crotonic acid, isocrotonic acid, angelic acid, tiglic acid and the water soluble salts of the aforesaid acids.

The telomers may additionally comprise proportions, usually minor proportions, of styrene, styrene-p-sulphonic acid, 2-acrylamido-2-methylpropane sulphonic acid, vinyl alcohol, vinyl acetate, vinyl chloride and/or acrylamide. The relative proportions of oligomer or polymer and the monomer may range from 1:1 to 1:1000, preferably from 1:5 to 1:500 especially 1:10 to 1:100, eg: 1:15 to 1:50. The reaction is preferably carried out in aqueous solution and most preferably using water soluble salts of the monomers, eg: at a pH greater than 5 especially 6 to 8. The preferred concentrations of the reagents in the reaction mixture is typically 50 to 80% by weight total solids especially 50 to 70%. The reaction, like the preparation of the intermediate requires a free radical source such as hydrogen peroxide and preferably elevated temperatures, eg: 40 to 100° C.

At the higher concentrations higher temperatures, eg: 100 to 140° C. more preferably 120 to 140° C. may be required to maintain a pourable solution. The molecular weight of the product is typically up to 200,000. Usually the number of monomer groups per molecule is from 1 to 500, eg: 10 to 100. To prepare the telomers we prefer pH between 2 and 9 especially 2 to 6, eg: 2.5 to 4.

We do not exclude the presence of water miscible solvents. The solvent should contain sufficient water to dissolve the reagents to a substantial extent. The organic solvent may for example comprise methanol, ethanol, isopropanol, ethylene glycol, propylene glycol, a water soluble oligomer of ethylene or propylene glycol such as diethylene glycol, a water soluble mono or di ether or ethylene glycol monomethyl ether, ethylene glycol dimethyl ether, diethylene glycol monoethyl ether or diethylene glycol mono methyl ether, glycerol, a water soluble glyceryl ether, acetone, and/or dioxan. The requirement to dissolve the reagents in the same aqueous based solvent is the main limitation on choice of unsaturated reagent. In cases of difficulty it may be possible to carry out the reaction in anhydrous dioxan.

The reaction may optionally be carried out in a stream of an inert gas such as nitrogen.

The reaction may be carried out batch-wise, semi-continuously or continuously, eg: in a pipe reactor. The free radical source may all be added initially or, preferably, in a plurality of additions, or continuously or semi-continuously throughout the reaction. To maximise the yield of phosphonated product it is sometimes necessary to add the unsaturated reagent, continuously or intermittently during the reaction period to an aqueous solution of the phosphinate.

The products especially telomers comprising acrylate and/or maleate and/or proportions, usually minor, or vinyl sulphonate, vinyl phosphonate and/or vinylidine diphosphonate are valuable as corrosion inhibitors and scale inhibitors in the treatment of water systems including boiler water, cooling water, eg: in evaporative cooling systems, process water, water in central heating and air conditioning systems.

The products are effective in the presence of chlorine, chlorine dioxide, bromine, hypochlorite, hypobromite and other oxidising biocides. They are useful in treatment of desalination plant and for treating water used or produced in oil wells including injection water, produced water and water used for hydrostatic testing of pipelines.

The product are also effective as a "smut" inhibitor or sealant in the anodising of aluminium, as additives to oral hygiene preparations and dentifrices and as a setting retarder for cement or plaster.

The products also find application as deflocculants or dispersants for particulate inorganic substances (such as clays and calcium carbonate) and for other pigments, for cement and for soils in detergency.

The products are also effective as corrosion inhibitors for ferrous and non-ferrous metals (e.g. aluminium or galvanised steel) and as a surface treatment for aluminium in the preparation of lithographic plates.

They are also of value as detergent builders or auxiliary builders, eg: in conjunction with zeolites, or as metal chelating agents, eg: in metal extractions.

The products are effective for the inhibition of scale caused by metal carbonates and basic carbonates (particularly those of metals of Group IIA of the Periodic Classification), as well as scale caused by carboxylates, fluorides, hydroxides, phosphates, phosphonates, silicates and sulphates.

They may be used in aqueous based functional fluids such as hydraulic fluids, lubricants, cutting fluids and oilfield drilling muds.

In particular, the telomers of the invention may be used in squeeze treatment of oil wells. They are especially effective in preventing barium sulphate scale. For example in oil wells the hole is typically flushed out with aqueous surfactant to provide a water wettable surface and then impregnated with a solution of the inhibitor. The calcium salt may be formed in situ either by calcium in the formation, where the latter comprises limestone, or by prior, or subsequent, treatment of the hole with an aqueous calcium salt, eg: where the formation comprises sandstone.

Effective concentrations may typically range from 1 to 200 ppm, eg: 1.5 to 20 ppm, most preferably 2 to 10 ppm, may give useful corrosion protection. However, for oilfield scale prevention where barium sulphate is a problem, concentrations in the range 5 to 200, especially 8 to 25, eg: 10 to 20 ppm, are preferred.

Products according to the invention may be used in combination with one another, and/or in conjunction with other water treatment agents including: surfactants, such as anionic surfactants (eg: $C_{10-20}$ alkyl benzene sulphonates, $C_{10-20}$ olefin sulphonates, $C_{10-20}$ alkyl sulphates, $C_{10-20}$ alkyl 1 to 25 mole ether sulphates, $C_{10-20}$ paraffinsulphonates, $C_{10-20}$ soaps, $C_{10-20}$ alkyl phenol sulphates, sulphosuccinates, sulphosuccinamates, lignin sulphonates, fatty ester sulphonates, $C_{10-20}$ alkyl phenol ether sulphates, $C_{10-20}$ alkyl ethanolamide sulphates, $C_{10-20}$ alpha sulphofatty acid salts, $C_{10-20}$ acyl sarcosinates, isethionates, $C_{10-20}$ acyl taurides, $C_{10-20}$ alkyl hydrogen phosphates), non-ionic surfactants (eg: ethoxylated material or synthetic $C_{8-25}$ alcohols, ethoxylated fatty acids, ethoxyl/propyleneoxy block copolymers, ethoxylated fatty amines, mono- and di-alkanolamides, amine oxides and $C_{10-20}$ acyl sorbitan and/or glyceryl ethoxylates) amphoteric surfactants (eg: betaines, sulphobetaines, and/or quaternised imidazoline), and/or cationic surfactants (eg: benzalkonium salts, $C_{10-20}$ alkyl trimethyl ammonium salts, and/or $C_{10-20}$ alkyl trimethyl or tris (hydroxymethyl) phosphonium salts); sequestrants, chelating agents, corrosion inhibitors and/or other threshold agents (eg: sodium tripolyphosphate, sodium ethylenediamine tetracetate, sodium nitrilo triacetate, tetra potassium pyrophosphate, acetodiphosphonic acid and its salts, ammonium trismethylene phosphonic acid and its salts, ethylenediamine tetrakis (methylene phosphonic) acid and its salts, diethylenetriamine pentakis (methylene phosphonic) acid, hexamethylenediamine tetrakis (methylene phosphonic) acid, bishexamethylenetriamine pentakis (methylene phosphonic) acid and ethanolamine bis(methylenephosphonic) acid and its salts); tolyltriazole and mixtures of nitrate, benzoate, HHP and/or PTCB) biocides (eg: tetrakis (hydroxymethyl) phosphonium salts, formaldehyde glutaraldehyde); oxidising biocides and/or bleaches (eg: chlorine, chlorine dioxide, hydrogen peroxide, sodium perborate); foam controlling agents such as silicone antifoams, acetylenic diols; oxygen scavengers such as hydrazines and/or hydroxylamines; pH controlling and/or buffering agents such as amines, borates citrates and/or acetates; chromium salts; zinc salts; and/or other water treatment agents such as polymeric dispersants and coagulants including polymaleic, polyacrylic and polyvinylsulphonic acids and their salts, starches and/or carboxy methyl cellulose and/or molybdates. The invention provides formulations comprising an effective amount of a product of the invention as aforesaid and any of the aforesaid known water treatment agents. Such formulations may, for example, contain from 5 to 95% by weight of a product of the invention and from 5 to 90% by weight of one or more of any of the aforesaid water treatment agents.

According to a further embodiment our invention provides a corrosion inhibiting pigment which is a solid composition which may be prepared by reacting a concentrated aqueous solution of any of the water soluble telomers according to the invention with a base or salt of calcium, zinc, barium, aluminium or other polyvalent metal and precipitating a solid salt.

According to a further embodiment our invention provides a corrosion inhibiting coating composition containing a pigment according to the invention.

The corrosion inhibiting pigment may be dissolved or dispersed in an anti corrosive paint, varnish, enamel, lacquer, or other coating formulation. The formulation may comprise a volatile liquid vehicle, such as water or a volatile organic solvent including petroleum spirit, turpentine, ketones, esters and/or aromatic hydrocarbon solvent, and/or a drying oil, such as linseed oil, soya oil, tung oil or dehydrated castor oil, which may optionally be dissolved in said volatile organic solvent or emulsified in said water.

The formation typically may also comprise a resin, eg: polyester, urea formaldehyde, melamine, acrylic, alkyd, polyurethane, vinyl chloride, vinyl acetate, phenolic or epoxy resin dissolved or dispersed therein and/or a dispersed pigment. We prefer that the pigment should be or should comprise other corrosion inhibiting pigments such as red lead, potassium zinc chromate, metallic zinc or aluminium powder or zinc oxide and/or that the formulation should contain one or more of the other corrosion inhibitors referred to above in addition to the corrosion inhibiting pigment of the invention.

The coating compositions may additionally contain any of the conventional paint ingredients, including pigments such as titanium oxide, iron oxide, carbon black, phthalocyanine pigments or aluminium stearate, chlorinated rubber, polystyrene, silicone, asphalt, wetting agents, dispersants, emulsifiers, biocides, flocculants, marine antifoulants, antifoams, viscosifiers, fire retardants, fluorescers, aerosol propellants, talc, clay and/or plasticisers.

Alternatively the water soluble corrosion inhibitors of the invention may be used to provide a corrosion inhibiting treatment for metal surfaces such as steel, aluminium and aluminium alloys after any machining and prior to storage, coating, electroplating, polishing or etching. Typically the work is coated with an aqueous solution containing at least an operative amount of said corrosion inhibitor, eg: 10 to 500 ppm preferably 25 to 300, eg: 20 to 200 especially 25 to 100, more especially 30 to 80.

After contacting with the corrosion, inhibiting solution the work may be rinsed and/or subjected to one or more coating or finishing operations such as resin coating, lacquering, enamelling, painting, electrophoretic coating, spattering, vapour deposition, electrodeposition, etching, chemical or electrical polishing or may be put aside for storage.

The work may be greased for storage, but an advantage of the treatment is that greasing and hence subsequent degreasing may be avoided.

The product may be incorporated into solid or liquid detergent compositions. It functions as a stain remover and also may help to stabilise any bleach present and exhibits valuable detergent building action by sequestering calcium. Typically it is added to detergent compositions in amounts of from 0.5 to 20% by weight of the composition. The liquid detergent of our invention preferably contains 5 to 50%, eg: 10 to 40% by weight surfactant, 5 to 60%, eg: 10 to 40% builder, 20 to 75%, eg: 50 to 70% by weight water and 0.1 to 2.5% of said polymer. The liquid detergent preferably also contains conventional amounts of minor adjuncts including enzymes, soil suspenders such as sodium carboxymethyl cellulose, optical brighteners, dyes, perfumes, preservatives and foam modifiers.

The builder preferably comprises non-phosphate builders such as zeolite, carbonate, citrate, nitrilotriacetate and ethylene diamine tetracetate.

The detergent formulations of the invention may contain from 1 to 90% by weight of surfactant, more usually 2 to 70%, eg: 3 to 60% especially 4 to 50%, preferably 5 to 40%, more preferably 6 to 30%, most preferably 7 to 20%.

For example the surfactant may be, or may comprise, one or more anionic surfactants such as an alkyl benzene sulphate, alkyl sulphate, alkyl ether sulphate, paraffin sulphonate, olefin sulphonate, alkyl ether sulphonate, alkylphenyl sulphate, alkylphenyl ether sulphate, alkyl sulphosuccinate, alkyl sulphosuccinamate, alkyl isethionate, alkyl sarcosinate, soap, alkyl ether carboxylate, alkyl ether polycarboxylate, alkyl tauride, alkyl phosphate, alkyl ether phosphate or alkyl or thiol capped polyelectrolytes such as an alkylthiol capped polymaleic acid.

All references to "alkyl" groups in this context refer to $C_{8-22}$ straight or branched chain alkyl or alkenyl groups. "Ether" refers to glyceryl, mono or poly ethylenoxy, mono or poly propyleneoxy. The cation of the aforesaid anionic surfactants is usually sodium but may be potassium or mono, di or tri alkylolamine. Less commonly the cation may, be lithium, ammonium, calcium, magnesium, zinc or a mono, di or tri alkyl amine such as isopropylamine or trimethylamine.

The surfactant may also be, or may comprise, one or more non-ionic surfactants such as the polyalkoxylated derivatives of alcohols carboxylic acids, alkyl phenols, alkylamines, alkanolamides, or glycerol or sorbitan ester, wherein each compound has an "alkyl" group as hereinbefore defined, and the polyalkylene oxy group comprises from 1 to 50, eg: 2 to 10 ethylene oxy groups.

The invention is illustrated by the following examples:

EXAMPLE 1

To a 1 liter round bottomed flask was added 132 g of hypophosphorous acid (50% w/w) and 1,4-dioxane (500 g), the mixture was heated under reduced pressure on a rotary evaporator to co-evaporate some of the water from the hypophosphorous acid. In total, 233 g of solvent were removed and this was replaced with 1,4-dioxane.

The solution from above was added to a 1 liter jacketed reactor fitted with a reflux condenser, temperature probe, gas sparge tube, outlet bubbler, oil circulator and overhead stirrer, and left under a gentle nitrogen sparge overnight.

The reaction mixture was heated to 70° C. and 2 g of fresh azoisobutyronitrile (AIBN) was added as the acetylene addition was started. Further 2 g portions were added every hour for 4 hours, after which the reaction was left to cool to room temperature and sparged with nitrogen for 16 hours, giving a 61% conversion to product.

A further 4 hours of acetylene addition with 2 g AIBN being added every hour resulted in a 68% yield of product; this was increased to 72% when sodium persulphate was added at a rate of 1 g per hour for 5 hours. At this point the reaction was concluded as being complete and was left to cool to room temperature under a nitrogen atmosphere. The product separated into two phases. Residual 1,4-dioxane was removed on the rotary evaporator and the product was diluted with water to 25% w/w.

Composition
Ethane 1,2-bis phosphinic acid 45.7% w/w
Diethylene triphosphinic acid 28.3% w/w
Hypophosphorous acid 18.6% w/w
Phosphate 7.7% w/w

EXAMPLE 2

To a 1 liter jacketed reactor fitted with a reflux condenser, temperature probe, oil circulator, overhead stirrer, and two peristaltic pumps was added 32.2 g of the reaction product of Example 1. The reaction mixture was heated to 78° C. after which the following two separate feeds were started at the same time:
1) 9 g of sodium persulphate in water 100 g
2) 72 g of acrylic acid in water (270 g) adjusted to pH4 with sodium hydroxide (46–48% w/w) and 32.2 g of the product of example 1.

The solutions were fed for 150 minutes and the temperature was steadily increased to 96° C. After the two feeds were complete they were immediately replaced with a further two feeds:
1) 9 g of sodium persulphate in water 100 g
2) 72 g of acrylic acid in water (270 g) adjusted to pH4 with sodium hydroxide (46–48% w/w).

The solutions were fed for 150 minutes and the temperature was maintained between 96 and 101° C. After the two feeds were complete the reaction mixture was left to stir for a further 60 minutes before being left to cool to room temperature. The product was a pale yellow solution (962 g), 98% conversion to polymeric products by $^{31}P$ NMR. GPC gave a molecular weight of 3650 g.

EXAMPLE 3

The product of Example 2 was tested in tube blocking tests as follows:

| Test Conditions | |
|---|---|
| Test Temperature | 121° C. |
| Test Medium | A synthetic Produced Water corresponding to a 50:50 mix of Formation Water:Sea Water and having the following composition |

| | IONIC COMPOSITION (mg/l) | | |
|---|---|---|---|
| ION | Formation Water | Sea Water | Produced Water |
| $Na^+$ | 24100 | 10890 | 17495 |
| $K^+$ | 1180 | 460 | 820 |
| $Ca^{2+}$ | 520 | 428 | 474 |
| $Mg^{2+}$ | 73 | 1368 | 720 |
| $Ba^{2+}$ | 650 | 0 | 325 |
| $Sr^{2+}$ | 55 | 7 | 31 |
| $Cl^-$ | 40400 | 19766 | 30083 |
| $SO_4^{2-}$ | 10 | 2960 | 1485 |
| $HCO_3^-$ | 0 | 140 | 70 |

| | |
|---|---|
| Test pH | The pH value is adjusted to 4.90 ± 0.05 @ 25° C. with 0.01 M acetic acid/sodium acetate buffer. |
| Inhibitor Concentration | The run starts with an initial inhibitor level of 100 mg/l (active acid) in the combined flow and decreases the concentration in 10 mg/l steps, with a complete tube cleaning and washing cycle being performed between each decrement. |
| Cycle Time | Each level of inhibitor is evaluated for 30 minutes before proceeding to the next, ie: lower evel. The pressure drop across the narrow bore coil is continuously monitored and logged by a personal computer running Advantech ® 'Genie' ™ data acquisition and control software. |
| Fail Criterion & MIC | In the absence of inhibitor and under these conditions, the tube becomes rapidly blocked with scale. In practice, to prevent complete and irrecoverable blockage of the tube, the brine flows are terminated and tube cleaning commences when the pressure drop reaches 1 psia. When evaluating inhibitors, if the pressure drop exceeds 1 psia within the 30 minutes |

-continued

Test Conditions cycle time, then the inhibitor is deemed to have failed at that level. The minimum inhibitory concentration, MIC therefore obviously lies somewhere between the "fail level" and the previous concentration at which the tube remained essentially clear for 30 minutes.

The product was effective at preventing tube blocking at concentrations down to between 80 and 90 ppm. This compares well with the best commercial oilfield scale inhibitors.

EXAMPLE 4

To a 250 ml 3-necked flask fitted with a reflux condenser, temperature probe and $N_2$ gas line was added 25 g sodium hypophosphite (0.7 mol $H_2O$), propargyl alcohol (14 g) and water (20 ml). Sodium persulphate (6 g) was dissolved with water (20 ml).

The reaction mixture was heated to reflux (approximately 101° C.) under an inert atmosphere and the initiator was steadily added through a peristaltic pump over 105 minutes, followed by a 30 minute age.

A further portion of initiator (6 g in 20 ml water) was added over 90 minutes followed by a 30 minute age. Analysis by $^{13}$C-NMR showed residual propargyl alcohol remained.

The reaction mixture was diluted with water (20 ml) to dissolve up the undissolved solids, a further portion of initiator (6 g in 20 ml water) was added over 90 minutes followed by a 30 minute age, after which the reaction was left to cool to room temperature.

Yield 150 g, 4% Actives.

| | Composition | |
|---|---|---|
| $^{31}$P-NMR shows | Polymeric product | 83.7% w/w |
| | Phosphorous acid | 11.4% w/w |
| | Phosphate | 2.7% w/w |
| | Sodium hypophosphite | 2.2% w/w |

$^{13}$C-NMR shows all propargyl alcohol reacted.

GPC gives MW of 1624: therefore "n" can be calculated as being 10.7.

EXAMPLE 5

To a 1l, four-necked flask fitted with a reflux condenser, temperature probe and $N_2$ gas line was added 107 g sodium hypophosphite (0.7 mol $H_2O$) propargyl alcohol (60 g) and water (85 ml). Sodium persulphate (26 g) was dissolved in water (85 ml).

The reaction mixture was heated to reflux (approximately 101° C.) under an inert atmosphere and the initiator was steadily added through a peristaltic pump over 120 minutes, followed by a 60 minute age.

$^{31}$P-NMR showed 41% sodium hypophosphite remained.

A further portion of initiator (26 g in 85 ml water) was added over 90 minutes followed by a 60 minute age.

The reaction mixture was diluted with water (100 ml) to dissolve up the undissolved solids and was left to cool to room temperature.

Yield 564 g, 27% Actives.

Composition

| | Composition | |
|---|---|---|
| $^{31}$P-NMR shows | Polymeric product | 84.1% w/w |
| | Phosphorous acid | 6.3% w/w |
| | Phosphate | 0.6% w/w |
| | Sodium hypophosphite | 9% w/w |

CPC gives MW of 1139, therefore "n" can be calculated as being 7.3.

EXAMPLE 6

The product of example 4 was tested as a corrosion inhibitor of mild steel in South Staffordshire water. The corrosion rate was less than 0.2 mils per year when the product was used at a concentration of 25 ppm.

What is claimed is:

1. A method of producing a compound of formula (II), wherein said method comprises co-polymerising hypophosphorous acid or a salt or ester of said acid with an acetylenic compound of formula RC≡CR', where R and R' are each hydrogen, and
wherein the compound of formula (II) is

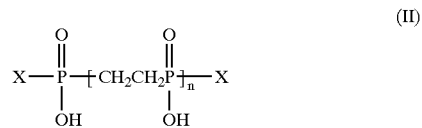

(II)

wherein X is hydrogen or a cation or an alkyl group and n is 1.05 to 100.

2. The method of claim 1, wherein said co-polymerisation is carried out in a solvent capable of dissolving both said hypophosphorous acid or salt and said acetylenic compound and in the presence of an initiator.

3. The method of claim 2, wherein said solvent is water.

4. The method of claim 2, wherein said solvent is a polar organic solvent selected from the group consisting of ethanol, dioxane, water-miscible glycols, glycol ethers, ketones and dimethyl formamide.

5. The method of claim 2, wherein said initiator comprises a source of free radicals.

6. The method of claim 2, wherein said initiator is selected from the group consisting of hydrogen peroxide, sodium persulphate, azo-compounds and organic peroxides.

7. The method of claim 2, wherein said initiator comprises a source of ultraviolet or ionising radiation.

8. The method of claim 1, wherein said co-polymerisation is carried out at a temperature of from 40 to 100° C.

9. The method of claim 8, wherein said temperature is from 50 to 70° C.

10. The method of claim 1, wherein both of said co-monomers are present in substantially equal proportions.

11. The method of claim 1, wherein either one of said co-monomers is present in a stoichiometric excess of up to 20% relative to the other co-monomer.

12. The method of claim 11, wherein said hypophosphorus acid co-monomer is present in a stoichiometric excess of up to 20% relative to said acetylenic co-monomer.

13. The method of claim 1, wherein said salt of hypophosphorous acid is selected from the group consisting of sodium hypophosphite, potassium hypophosphite and ammonium hypophosphite and said ester of hypophosphorous acid is selected from the group consisting of methyl hypophosphite, ethyl hypophosphite and isopropyl hypophosphite.

14. A compound consisting essentially of a telomer of the formula (III):

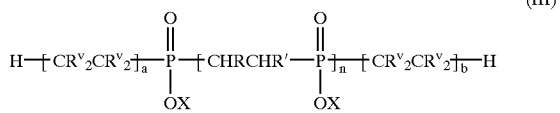 (III)

wherein X is hydrogen or a cation,

R and R' are each independently selected from the group consisting of hydrogen, hydroxyl, carboxyl, alkyl, aryl, alkaryl, hydroxy-substituted alkyl, aryl or alkaryl and carboxy-substituted alkyl, aryl or alkaryl, provided that R and R' together have a total of less than 23 carbon atoms, at least one $R^v$ in each monomer unit is selected from the group consisting of hydroxy, carboxy, sulpho, phosphono, amido, aceto, aryl and halogen;

each other $R^v$ is independently selected from the group consisting of hydrogen, $C_{1-4}$, alkyl, carboxyl, sulpho, phosphono, hydroxyl groups, carboxy-substituted, sulpho-substituted, phosphono-substituted and hydroxy-substituted $C_{1-4}$ alkyl groups;

(a+b) is in the range 5 to 200 and n is greater than 1; and wherein said compound is made under aqueous conditions and in the presence of a free radical initiator.

15. A method of producing the telomer of claim 14, said method comprising co-polymerising a polymer of formula II with at least one monomer of formula $CR^v{}_2=CR_2{}^v$, wherein $R^v$ has the same meaning as in claim 14, in aqueous conditions and in the presence of a free-radical initiator; and wherein Formula (II) is:

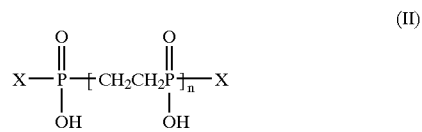 (II)

wherein X is hydrogen or a cation or an alkyl group and n is 1.05 to 100.

16. The method of claim 15, wherein said at least one monomer is selected from the group consisting of acrylic acid, fumaric acid, maleic acid, vinylsulphonic acid, vinyl phosphonic acid, vinylidene diphosphonic acid, methacrylic acid, itaconic acid, aconitic acid, mesaconic acid, citraconic acid, crotonic acid, isocrotronic acid, angelic acid, tiglic acid and the water-soluble salts of said acids.

17. The method of claim 15, wherein the relative proportions of said polymer and said at least one monomer are in the range 1:1 to 1:1000.

18. The method of claim 17, wherein said relative proportions are in the range 1:5 to 1:500.

19. The method of claim 17, wherein said relative proportions are in the range 1:10 to 1:100.

20. The method of claim 17, wherein said relative proportions are in the range 1:15 to 1:50.

21. The method of claim 15, wherein said co-polymerisation is carried out in aqueous solution.

22. The method of claim 21, wherein said co-polymerisation is carried out in the presence of a water-miscible solvent selected from the group consisting of methanol, ethanol, isopropanol, ethylene glycol, propylene glycol, diethylene glycol, ethylene glycol monomethyl ether, ethylene glycol dimethyl ether, diethylene glycol monomethyl ether, glycerol, water-soluble glyceryl ethers, acetone and dioxane.

* * * * *